(12) United States Patent
Chao et al.

(10) Patent No.: US 12,740,705 B2
(45) Date of Patent: Sep. 22, 2026

(54) WEARABLE BIOLOGICAL DATA PPG SENSOR WITH FLEXIBLE PRINTED CIRCUIT PATCH HAVING RECHARGABLE BATTERY

(71) Applicant: National Yang Ming Chiao Tung University, Hsinchu (TW)

(72) Inventors: Paul C.-P. Chao, Taipei City (TW); Yung-Hua Kao, Taoyuan City (TW); Yan-Wei Chen, Taipei City (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 814 days.

(21) Appl. No.: 17/878,520

(22) Filed: Aug. 1, 2022

(65) Prior Publication Data

US 2023/0045202 A1 Feb. 9, 2023

(30) Foreign Application Priority Data

Aug. 4, 2021 (TW) ................................ 110128799

(51) Int. Cl.
*A61B 5/00* (2006.01)

(52) U.S. Cl.
CPC .............. *A61B 5/0002* (2013.01); *A61B 5/72* (2013.01)

(58) Field of Classification Search
CPC ....... A61B 5/0002; A61B 5/72; A61B 5/6824; A61B 5/6833; A61B 2560/0214; A61B 5/02438; A61B 5/02433
See application file for complete search history.

(56) References Cited

U.S. PATENT DOCUMENTS 9,664,556 B2 5/2017 Chu et al.
10,627,783 B2 4/2020 Rothkopf et al.
(Continued)

FOREIGN PATENT DOCUMENTS

TW 201629520 A 8/2016
TW 201732467 A 9/2017

*Primary Examiner* — Serkan Akar
(74) *Attorney, Agent, or Firm* — Birch, Stewart, Kolasch & Birch, LLP

(57) ABSTRACT

The present invention is related to a biological data sensor for measuring biological data from a user. The biological data sensor comprises a sensing module and a wearable charging module. The sensing module is formed by flexible printed circuit (FPC) and attached to the user's skin. The sensing module includes light emitting units, at least one sensing unit, and a rechargeable battery. The light emitting unit emits a first sensing light onto the user's skin. The first sensing light is transmitted onto the user's skin and reflected from the user's skin as a second detecting light. The sensing unit receives the second sensing light and outputs the biological data. The rechargeable battery is electrically connected to the light emitting units and the sensing unit, and the rechargeable battery provides power to the light emitting units and the sensing unit. The wearable charging module is worn on a part of the user adjacent to the sensing module. The wearable charging module includes a charger and a first transmitter. The first transmitter is electrically connected to the charger, obtains power from the charger, wirelessly transmits the power to the rechargeable battery of the sensing module, and receives the biological data from the sensing module.

12 Claims, 3 Drawing Sheets

100

(56) References Cited

U.S. PATENT DOCUMENTS

| | | | | |
|---|---|---|---|---|
| 11,116,448 | B1 * | 9/2021 | Trapero Martin | A61B 5/0816 |
| 2014/0375465 | A1 * | 12/2014 | Fenuccio | H05K 7/02 361/679.01 |
| 2016/0106367 | A1 * | 4/2016 | Jorov | A61B 5/02416 600/407 |
| 2017/0135636 | A1 * | 5/2017 | Park | H04W 4/027 |
| 2018/0020956 | A1 | 1/2018 | Lee et al. | |

* cited by examiner

WEARABLE BIOLOGICAL DATA PPG SENSOR WITH FLEXIBLE PRINTED CIRCUIT PATCH HAVING RECHARGABLE BATTERY

FIELD OF THE INVENTION

The disclosure is related to a sensor, in particular, a biological data sensor.

BACKGROUND OF THE INVENTION

With the advancement of technology, wearable smart devices such as smart watches and/or smart bracelets that can detect biological data such as pulse have been applied widely in people's daily life so that they can monitor their own physical conditions. However, the above wearable smart devices may move when the user walks or runs, which further affects the sensing result. Hence, providing a more accurate biological data sensing function is still one of the problems to be solved in the art.

SUMMARY OF THE INVENTION

The biological data sensor according to the disclosure can effectively acquire a user's biological data for a long time.

In an embodiment, the biological data sensor for measuring biological data from a user. The biological data sensor comprises the sensing module and the wearable charging module. The sensing module is formed by flexible printed circuit (FPC) and attached on the user's skin. The sensing module includes a plurality of light emitting units, at least one sensing unit, and a rechargeable battery. The light emitting unit emits a first sensing light onto the user's skin. The first sensing light is transmitted onto the user's skin and reflected from the user's skin as the second detecting light. The sensing unit receives the second sensing light and outputs the biological data. The rechargeable battery is electrically connected to the light emitting units and the sensing unit, and the rechargeable battery provides power to the light emitting units and the sensing unit. The wearable charging module is worn on a part of the user adjacent to the sensing module. The wearable charging module includes a charger and a first transmitter. The first transmitter is electrically connected to the charger, obtains power from the charger, wirelessly transmits the power to the rechargeable battery of the sensing module, and receives the biological data from the sensing module.

In an embodiment, the sensing unit includes receiving units and a data retrieving unit. The receiving units receive the second sensing light and provide a light-sensing signal. The data retrieving unit is electrically connected to the receiving units, and the data retrieving unit retrieves the biological data from the light-sensing signal.

In an embodiment, the data retrieving unit retrieves the biological data by photoplethysmography.

In an embodiment, the receiving unit comprises an organic photo sensor (OPS).

In an embodiment, the receiving units are grouped into a plurality of sensing arrays, and the light emitting units are arranged around each of the sensing arrays.

In an embodiment, the sensing module further includes a second transmitter. The second transmitter is electrically connected to the rechargeable battery and the sensing unit, wherein biological data and power may be wirelessly transmitted between the first transmitter and the second transmitter.

In an embodiment, the second transmitter includes a second power transmitter and a second data transmitter. The second power transmitter is configured to wirelessly transmit power. The second data transmitter is configured to wirelessly transmit the biological data.

In an embodiment, the first transmitter includes a first power transmitter and a first data transmitter. The first power transmitter is configured to wirelessly transmit power. The first data transmitter is configured to wirelessly transmit the biological data.

In an embodiment, the light emitting unit includes at least one organic light-emitting diode.

In an embodiment, the sensing module may be attached onto the user's skin adjacent to the user's wrist, and the wearable charging module may be worn on the user's wrist.

In an embodiment, the charger includes a solar cell.

In an embodiment, the biological data sensor further comprises a control device. The control device may be electrically connected to a wearable charging module in a wired or wireless manner. The control device includes a third transmitter and a display. The third transmitter is configured to receive the biological data and power information from the first transmitter. The display is configured to display the biological data and the power information.

In an embodiment, the control device is a desktop computer, a laptop computer, or a smart phone.

In an embodiment, the sensing module is a patch.

Accordingly, the biological data sensor according to the disclosure can provide, by the sensing module and the portable charging module, a long-term sensing function for biological data.

DETAILED DESCRIPTION OF THE PREFERRED EMBODIMENTS

The biological data sensor according to the disclosure can be used to read a user's biological data for a long time. Preferably, the biological data sensor according to the disclosure can sense the pulse of the user (that is, sensing the arterial pulse on the user's skin surface). For example, the biological data sensor according to an embodiment of the invention can be used to sense the pulse of the radial artery of the wrist, or the pulse of the limbs and/or other parts suitable for wearing portable devices.

Figure 1A:
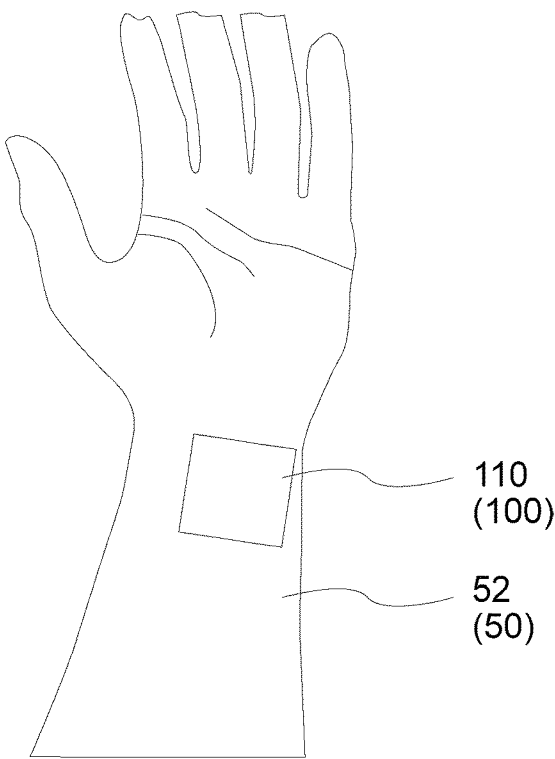
FIG. 1A is a schematic of the sensing module of the biological data sensor according to an embodiment of the disclosure.

FIG. 1A is a schematic of the sensing module of the biological data sensor according to an embodiment of the disclosure. Refer to FIG. 1A. In an embodiment of the disclosure, the biological data sensor 100 is suitable for measuring biological data from the user 50. The biological data sensor 100 is attached to the skin of the wrist 52 of the user 50. For example, the sensing module 110 of the embodiment is attached to the skin of the wrist 52 of the user 50 adjacent to the radial artery. Therefore, the sensing module 110 will obtain more accurate sensing results when acquiring the biological data of the user 50.

Figure 1B:
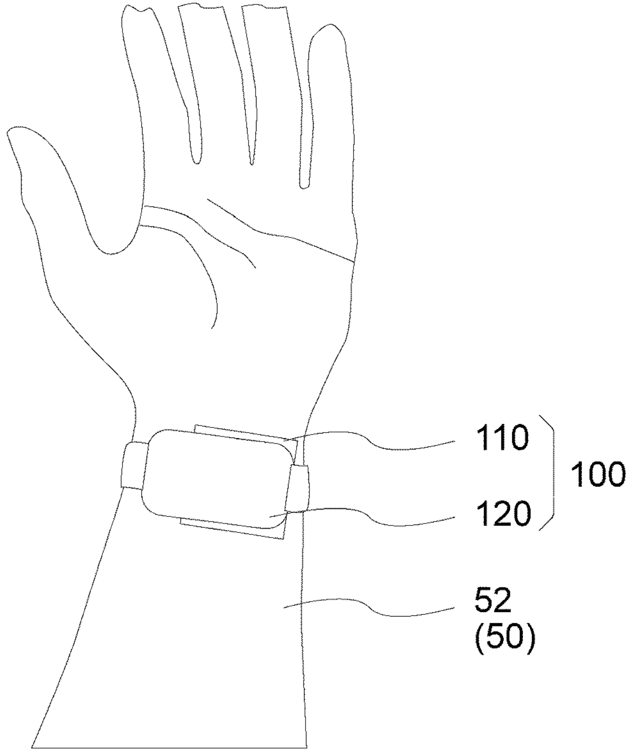
FIG. 1B is a schematic of the sensing module and the wearable charging module of the biological data sensor according to an embodiment of the disclosure.

FIG. 1B is a schematic of the sensing module and the wearable charging module of the biological data sensor according to an embodiment of the disclosure. Refer to FIG. 1B. In the embodiment, the biological data sensor 100 comprises the sensing module 110 and the wearable charging module 120. Wherein the sensing module 110 can be attached to the skin of the wrist 52 of the user 50; the wearable charging module 120 can be worn on a part of the user 50 adjacent to the sensing module 110. For example, the wearable charging module 120 according to the embodiment can be worn on the wrist 52 of the user 50 adjacent to the sensing module 110. However, the invention of the disclosure is not limited to the aforementioned embodiment. In other embodiments, the sensing module 110 can be attached to other locations, and the wearable charging module 120 can be worn on a part of the user 50 adjacent to the other locations mentioned above.

Figure 2A:
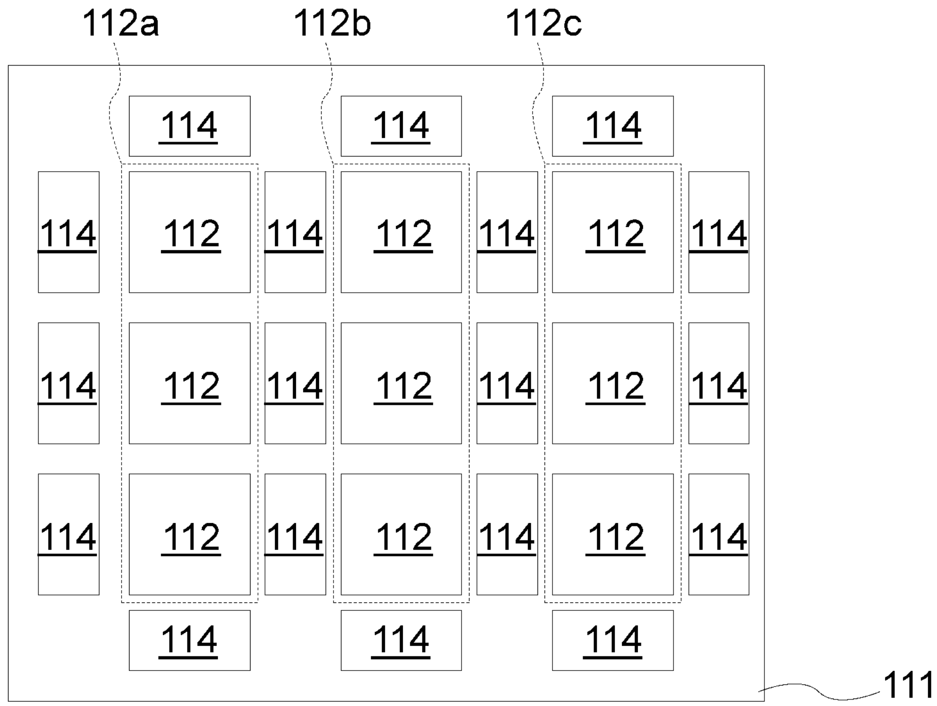
FIG. 2A is a schematic of the sensing module according to an embodiment of the disclosure.

FIG. 2A is a schematic of the sensing module according to an embodiment of the disclosure. Refer to FIG. 2A. In the aforementioned embodiment, the sensing module 110 comprises a plurality of light emitting units 114 and the sensing unit 112. Wherein the light emitting units 114 emit light onto a side of the sensing module 110, and the sensing unit 112 receives light at the same side of the light emitting units 114. More specifically, both of the light emitting units 114 and the sensing unit 112 of the sensing module 110 can emit sensing light or receive sensing light onto/from the skin that the sensing module 110 is attached to.

Furthermore, the sensing module 110 according to the embodiment can be, formed by flexible printed circuit (FPC), but not limited thereto. The light emitting units 114 can be, for example, solid light sources such as light emitting diode (LED). The light emitting units 114 are preferably, but not limited to, organic light emitting diode (OLED) for providing wider illuminating effect of the sensing light. The sensing light emitted by the light emitting units 114 can be, but is not limited to, red light, green light or infrared light. The sensing unit 112 can be, for example, organic photo sensor for receiving the sensing light reflected from the skin of the wrist 52 of the user 50.

On the other hand, in an embodiment, the sensing units 112 can be grouped into a plurality of sensing arrays 112*a* to 112*c*, and the light emitting units 114 are arranged around each of the sensing arrays 112*a* to 112*c* to provide a more specific sensing effect.

In detail, in an embodiment of the presented invention, the light emitting units 114 may emit light with different colors according to different application scenarios. For example, the light emitting units 114 adjacent to the sensing array 112*a* and the sensing array 112*c* may emit red light, and the light emitting units 114 adjacent to the sensing array 112*b* may emit green light. However, the present invention of the disclosure is not limited thereto. Since the sunlight contains infrared, when red light or infrared light is used to measure pulse, it is easy to be affected by outdoor ambient light. But when green light is used, it is not as easy to be affected by outdoor ambient light. Therefore, in an embodiment, the sensing module 110 can have the light emitting units 114 emit red light or green light depending on the application scenario. For example, when the measurement is taken indoors, the light emitting unit 114 will use red light; when the measurement is taken outdoors, the light-emitting unit 114 will use green light. In addition, in an embodiment, due to the high light absorption rate of the erythrocyte when the user is in a moving state, the light emitting unit 114 emitting red light can be selected for sensing when the user of the sensing module 110 is in a static state, and the light emitting unit 114 emitting green light can be selected for sensing when the user of the sensing module 110 is in a moving state. On the other hand, because red light is more penetrating than green light on human body, red light can respond to changes in human body characteristics more accurately than green light. As such, in an embodiment, light emitting units 114 of different light color can be selected depending on the needs of the measurement scenarios (for example, skin color and/or measurement location).

Figure 2B:
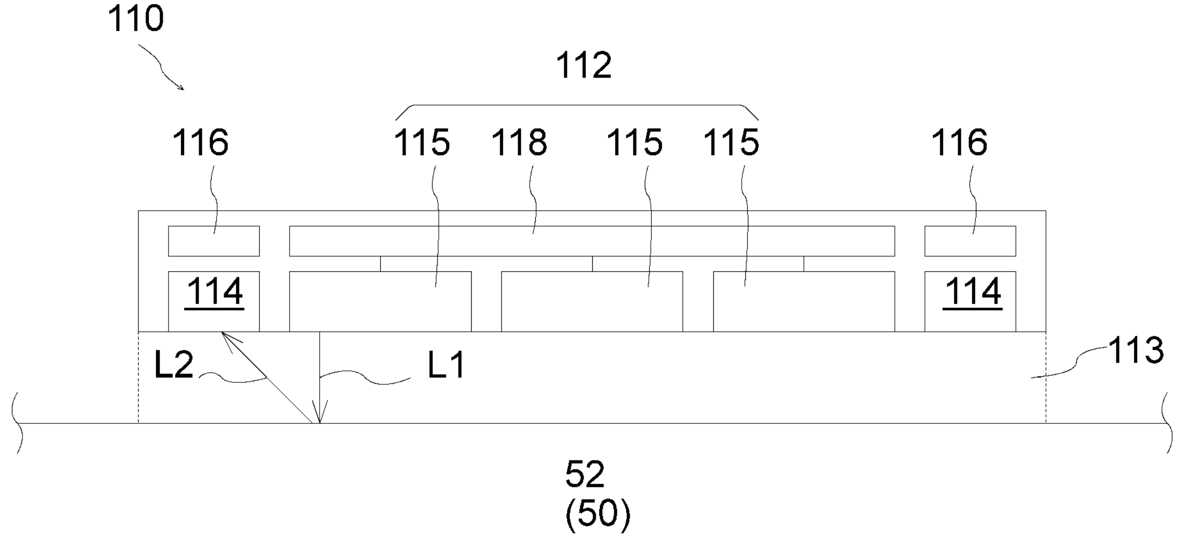
FIG. 2B is a side view of the sensing module according to an embodiment of the disclosure.

FIG. 2B is a side view of the sensing module according to an embodiment of the disclosure. Refer to FIG. 2B. The sensing module 110 can be, for example, attached to the wrist 52 of the user 50 by the adhesive layer 113. The sensing module 110 can be, but is not limited to, a patch. It should be noted that the thickness of a part of the components illustrated in FIG. 2B is enlarged for illustration purposes. The scope of the disclosure is not limited by the scale of the components illustrated in FIG. 2B.

In the sensing module 110 according to the aforementioned embodiment, the light emitting units 114 emits the first sensing light L1 onto the user 50's skin. The first sensing light L1 is transmitted onto the user 50's skin and reflected from the user 50's skin as the second sensing light L2. The sensing unit 112 receives the second sensing light L2 and outputs the biological data.

More specifically, the sensing module of the embodiment further comprises the rechargeable battery 116. The rechargeable battery 116 is electrically connected to the light emitting units 114 and the sensing unit 112. The rechargeable battery 116 provides required power to the light emitting unit 114 and the sensing unit 112. In the embodiment, the rechargeable battery 116 includes, for example, a power storage component and a wireless charging coil. Wherein the power storage component is configured to store power, and the wireless charging coil is configured to acquire power from the wearable charging module 120 mentioned above in a manner of wireless charging. However, the presented invention of the disclosure is not limited thereto.

On the other hand, the sensing unit 112 of the sensing module 100 further includes a plurality of receiving units 115 and the data retrieving unit 118. The receiving units 115 are electrically connected to the data retrieving unit 118. The data retrieving unit 118 is, for example, a photoplethysmography reading circuit. In other words, the data retrieving unit 118 retrieves the biological data by photoplethysmography. The receiving units 115 receive the second sensing light L2 and provide a light sensing signal. The data retrieving unit 118 is electrically connected to the receiving units 115 and retrieves the biological data from the light sensing signal. Wherein the biological data can include the user's blood pressure, blood flow velocity, or heartbeats per unit time.

Furthermore, the data retrieving unit 118 can recognize preferred biological data from the light sensing signal provided by the receiving units 115. For example, in a skin area with higher blood flow volume, the second sensing light will have a higher degree of variation. Therefore, the data retrieving unit 118 can select the light sensing signal with the maximum variation to retrieve biological data.

Figure 3A:
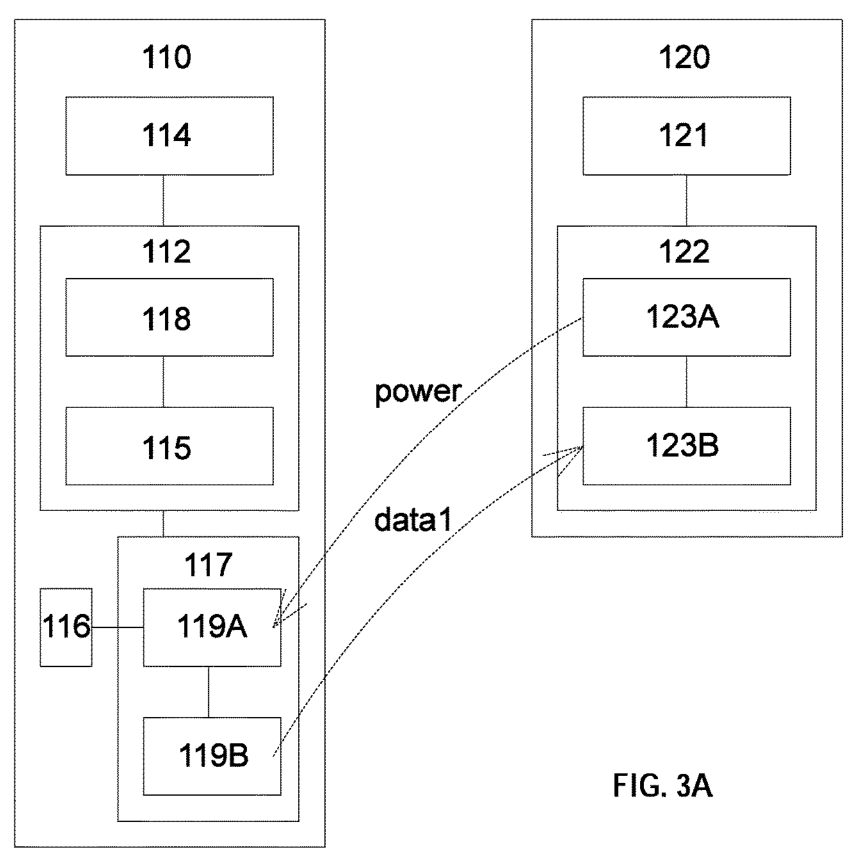
FIG. 3A is a schematic of the sensing module according to an embodiment of the disclosure.

FIG. 3A is a schematic of the sensing module according to an embodiment of the disclosure. Refer to FIG. 3A, the biological data sensor 100 comprises the sensing module 110 and the wearable charging module 120. The sensing module 110 attached to the user comprises the light emitting unit 114, the sensing unit 112, the rechargeable battery 116 and the second transmitter 117. The wearable charging module 120 worn on the part of the user adjacent to the sensing module 110 comprises the charger 121 and the first transmitter 122.

In the embodiment, the first transmitter 122 is electrically connected to the charger 121. The first transmitter 122 obtains power from the charger 121, transmits the power to the rechargeable battery 116 of the sensing module 110, and receives biological data (data1) from the sensing module 110. More specifically, the charger 121 includes, for example, components that can generate power or obtain power from outside. The charger 121 preferably includes solar power generating unit (for example, solar cell). Hence, the wearable charging module 120 can obtain power via the charger 121, and transmit power via the first transmitter 122.

In addition, the sensing unit 112 according to the embodiment includes the receiving unit 115 and the data retrieving unit 118 configured to receive the second sensing light mentioned above and derive biological data. The second transmitter 117 is electrically connected to the rechargeable battery 116 and the sensing unit 112. Wherein the biological data (data1) and the electrical power are wirelessly transmitted between the first transmitter 122 and the second transmitter.

In detail, in the sensing module 110 according to the embodiment, the second transmitter includes the second electrical power transmitter 119A and the second data transmitter 119B, the second electrical power transmitter 119A is configured to wirelessly transmit electrical power. The second data transmitter 119B is configured to wirelessly transmit the biological data (data1).

In the embodiment, the first transmitter 122 of the wearable charging module 120 includes the first power transmitter 123A and the first data transmitter 123B. The first power transmitter 123A is configured to wirelessly transmit the electrical power. The first data transmitter 123B is configured to wirelessly transmit the biological data (data1).

Figure 3B:
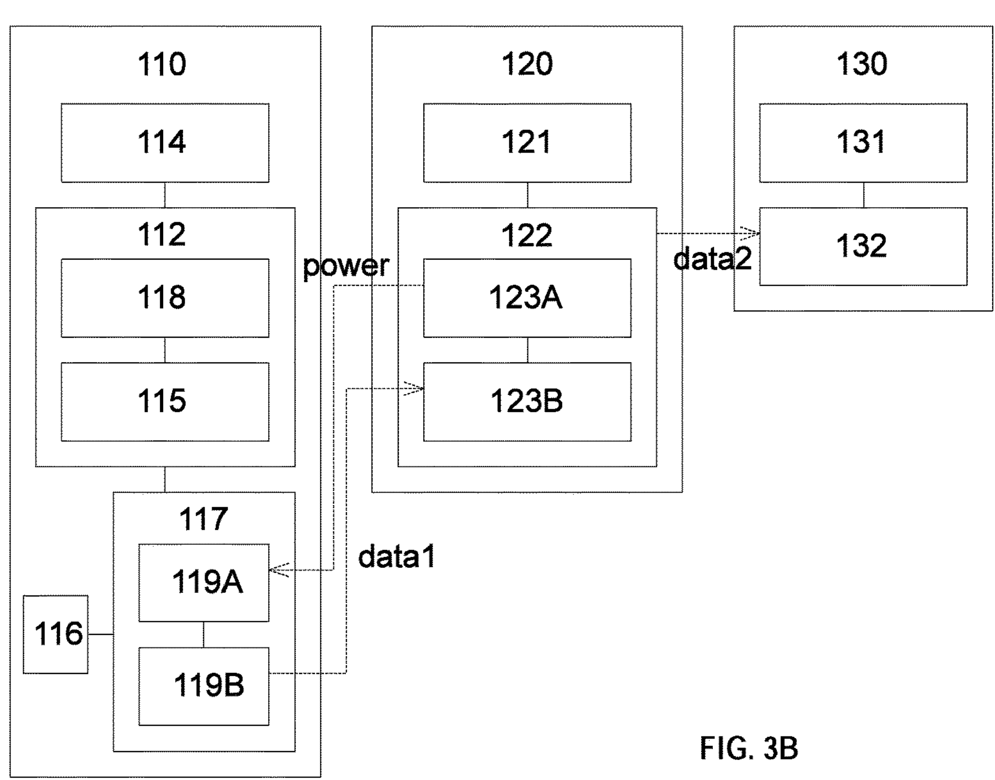
FIG. 3B is a schematic of the sensing module according to an embodiment of the disclosure.

On the other hand, the biological data sensor 100 according to the embodiment may further comprise the control device 130. FIG. 3B is a schematic of the sensing module according to an embodiment of the disclosure. In the biological data sensor 100 according to the embodiment mentioned above, the control device 130 is electrically connected to the wearable charging module 120 in a wired or wireless manner. Preferably, the control device 130 is, for example, a laptop computer or a smart phone. The control device 130 is, for example, connected to the wearable charging module 120 via Bluetooth to transmit information to/from the wearable charging module 120. The present invention is not limited by the type of control device mentioned above. In other embodiments, the control device can also be a desktop computer.

In detail, in the aforementioned embodiment, the control device 130 includes the third transmitter 132 and the display 131. The third transmitter 132 is configured to receive information (data2) from the first transmitter 122. The information (data2) can include biological data or power information. Wherein the biological data corresponds to the biological data acquired by the sensing module 110. The power information corresponds to the charging state of the charger 121, the amount of electricity in the rechargeable battery 116, or the connection status between the first power transmitter 123A and the second transmitter 119A, but the present invention is not limited thereto. The display 131 is configured to display the biological data and the power information mentioned above to help the user further understand, via a laptop computer or a smart phone, the status of the biological data sensor 100 and the sensing results. The display 131 can also be configured to remind the user whether he/she needs to move the wearable charging module 120 according to the connection status to maintain the quality of the biological signal detection provided by the biological data sensor 100.

In summary of the above, the biological data sensor proposed by the invention can be attached to the user's skin via a sensing module, obtain power from outside through the portable charging module, and then provide power to the sensing module through wireless charging, so as to provide a long-term biological data sensing function.

What is claimed is:

1. A biological data sensor for measuring biological data from a user, the biological data sensor comprising:

a sensing module as a patch, formed by flexible printed circuit (FPC), attached on the user's skin, the sensing module including:

a photoplethysmography;

light emitting units emitting a first sensing light to the user's skin, the first sensing light transmitted to the user's skin and reflected from the user's skin into a second sensing light;

at least one sensing unit receiving the second sensing light and outputting the biological data; and a rechargeable battery electrically connected to the light emitting units and the sensing unit, the rechargeable battery providing power to the light emitting units and the sensing unit; and a wearable charging module worn on a portion of the user adjacent to the sensing module, the wearable charging module including:

a charger; and a first transmitter electrically connected to the charger, the first transmitter obtaining power from the charger, wirelessly transmitting the power to the rechargeable battery of the sensing module, and receiving the biological data from the sensing module, wherein the wearable charging module is configured to wirelessly transmit the power to the rechargeable battery while the sensing module remains attached to the user's skin and without removing the sensing module from the user.

2. The biological data sensor of claim 1, wherein the sensing unit includes:

receiving units receiving the second sensing light and providing a light-sensing signal; and a data retrieving unit electrically connected to the receiving units, the data retrieving unit retrieving the biological data from the light-sensing signal.

3. The biological data sensor of claim 2, wherein the data retrieving unit retrieves the biological data by photoplethysmography.

4. The biological data sensor of claim 2, wherein the receiving units are grouped into a plurality of sensing arrays, and the light emitting units are arranged around each of the sensing arrays.

5. The biological data sensor of claim 1, wherein the sensing module further includes:

a second transmitter electrically connected to the rechargeable battery and the sensing unit, wherein the first transmitter and the second transmitter are adapted to wirelessly transmit the biological data and power between the first transmitter and the second transmitter.

6. The biological data sensor of claim 5, wherein the second transmitter includes:

a second power transmitter configured to wirelessly transmit power; and a second data transmitter configured to wirelessly transmit the biological data.

7. The biological data sensor of claim 1, wherein the first transmitter includes:

a first power transmitter configured to wirelessly transmit power; and a first data transmitter configured to wirelessly transmit the biological data.

8. The biological data sensor of claim 1, wherein the light emitting unit includes at least one organic light-emitting diode.

9. The biological data sensor of claim 1, wherein the sensing module is adapted to be attached on the user's skin adjacent to the user's wrist, and the wearable charging module is adapted to be worn on the user's wrist.

10. The biological data sensor of claim 1, wherein the charger includes a solar cell.

11. The biological data sensor of claim 1, further comprising:

a control device adapted to electrically connect to the wearable charging module in a wired or wireless manner, wherein the control device includes:

a third transmitter configured to receive the biological data and power information from the first transmitter; and a display configured to display the biological data and the power information.

12. The biological data sensor of claim 11, wherein the control device is a desktop computer, a laptop computer, or a smart phone.

* * * * *